United States Patent
Goodridge

(10) Patent No.: US 7,276,332 B2
(45) Date of Patent: Oct. 2, 2007

(54) BACTERIOPHAGE LINKED IMMUNOSORBENT ASSAY FOR RAPID, SENSITIVE DETECTION OF MULTIPLE ANALYTES

(75) Inventor: Lawrence Goodridge, Ft. Collins, CO (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 11/438,982

(22) Filed: May 23, 2006

(65) Prior Publication Data
US 2007/0054292 A1    Mar. 8, 2007

Related U.S. Application Data

(60) Provisional application No. 60/683,613, filed on May 23, 2005.

(51) Int. Cl.
*C12Q 1/00* (2006.01)

(52) U.S. Cl. .......................................................... 435/4

(58) Field of Classification Search ..................... None
See application file for complete search history.

(56) References Cited

OTHER PUBLICATIONS

Hazel, T.G., "Rapid, Ultra-Sensitive Detection of *E. coli* 0157:H7", Scientific Conf. Abstract, Dept. of Marketing, Innovative Biosensors, Inc. 2005.
Petrenko, V.A. & Vodyanoy, V.J., "Phage Display for Detection of Biological Threat Agents", Journal of Microbiological Methods, 53, 2003, 253-262.
Emanuel, P.A., Dang, J., Gebhardt, J.S., et al., "Recombinant Antibodies: A new Reagent for Biological Agent Detection", Biosensors & Bioelectronics, 14, 2000, 751-759.
Gough, K.C., Cockburn, W., & Whitelam, G.C., "Selection of Phage-Display Peptides that Bind to Cucumber Mosaic Virus Coat Protein", Journal of Virological Methods, 79, 1999, 169-180.
Rider, T.H., Petrovick, M.S., Nargi, F.E., et al. "A B Cell-Based Sensor for Rapid Identification of Pathogens", Science, 301, Jul. 11, 2003, 213-215.

*Primary Examiner*—Bruce R. Campell
*Assistant Examiner*—Nicole E Kinsey
(74) *Attorney, Agent, or Firm*—Kent A. Herink; Emily E. Harris

(57) ABSTRACT

The invention is a method for the development of a platform that enables the efficient and simultaneous creation of multiple detection assays. The invention entails the use of any bacteriophage, modified to carry a reporter gene, to which any analyte-recognizing moiety is attached via the capsid. The modified bacteriophage is used to attach to the target analyte. This attachment is identified via bacteriophage amplification in a helper bacteria strain with subsequent production and detection of the reporter gene.

4 Claims, 1 Drawing Sheet

BACTERIOPHAGE LINKED IMMUNOSORBENT ASSAY FOR RAPID, SENSITIVE DETECTION OF MULTIPLE ANALYTES

This application claims priority to U.S. Patent Application Ser. No. 60/683,613, filed May 23, 2005.

BACKGROUND OF THE INVENTION

The invention relates generally to methods of detecting target analytes and, more specifically, the development of a platform that enables the efficient and simultaneous creation of multiple detection assays and the use of such assays to detect a wide variety of target analytes, including biomolecules.

All immunoassays, regardless of their format or usage, require a reliable and sensitive detection system. The most sensitive immunoassays are radioimmunoassays. However, the ELISA is the most widely used. ELISA assays rely on enzyme-catalyzed detection, and typically employ calorimetric substrates that result in color formation. The enhanced sensitivity enabled by the BALISA will greatly improve the quality of immunologically based tests. The sensitive detection afforded by the BALISA offers other advantages over existing technologies. If one chooses to trade off sensitivity for a shorter assay time period, use of ultra-sensitive detection technology enables faster measurement of analytes. Finally, ultra-sensitive detection technology enables one to further dilute difficult samples such as meat. This improved sensitivity is especially critical in the detection of biomolecules which may be present in low concentrations, such as prions or microorganisms that have a very slow generation time, such as *Mycobacterium tuberculosis*.

The invention entails the use of any bacteriophage, modified to carry a reporter gene, to which any analyte-recognizing moiety is attached via the capsid. The modified bacteriophage is used to attach to the target analyte. This attachment is identified via bacteriophage amplification in a helper bacteria strain with subsequent production and detection of the reporter gene. Assays according to the present invention are able to detect rapidly and with high sensitivity a large variety of biomolecules, including bacteria, viruses, toxins, bioterrorist agents such as anthrax spores, and prions.

The advantages of this system over other systems are numerous. One important advantage is sensitivity. The detection aspect of this assay is based on phage replication and enzymatic cleavage of a substrate and thus has two built-in signal amplification steps. Many bacteriophages can bind to a single target analyte. Consequently, the sensitivity of this assay is superior to other methods because as few as 100-1000 phages would be able to produce a detectable signal. In practical terms, this means that the system should be able to directly detect 10-100 particles of the target analyte, and the actual detection number is expected to be lower than that, as more than one bacteriophage will bind to a single analyte particle.

In addition, the method described here, in which multiple assays can be produced from a single bacteriophage, is advantageous and cost effective because the assays can be produced based on a standardized platform, without the need to genetically and phenotypically completely characterize new bacteriophages for every new test.

The assay combines two proven methods, reporter bacteriophage technology, and Enzyme linked Immunosorbent Assay (ELISA) into one integrated method. The integrated technology, known as the Bacteriophage Linked Immunosorbent Assay (BALISA) harnesses the signal amplification produced by bacteriophage amplification, and enzymatic cleavage of a substrate to produce a very sensitive assay, capable of rapid detection of the target biomolecule. In one specific use, the BALISA test described herein could be used to detect foodborne pathogens. Foodborne illness accounts for seventy-five million illnesses in the United States each year. In another use, the BALISA could be used to detect biological and chemical select agents, capable to be used as biological weapons. These agents include toxins, bacteria, and viruses. The BALISA can be used directly in the field, thereby allowing fast, sensitive detection of pathogenic microorganisms and toxins.

SUMMARY OF THE INVENTION

The invention provides methods for detecting one or more target analytes in a sample relying in part on phage amplification. In a preferred embodiment, a phage modified to carry a reporter gene and to which has been attached an analyte-recognizing moiety is added to the sample. The analyte-recognizing moiety binds to the analyte. A helper strain of a microorganism susceptible to infection by the phage is added and a substrate that provides a signal in response to the reporter molecule are added. The phage replicates inside the microorganism producing the reporter molecule. The cells of the microorganism are then lysed to release the reporter molecules into the substrate and the presence or absence of the target analyte is detected. Under certain conditions, as an alternative to lysing the cells, the phage is allowed to replicate until the microorganisms burst and release the reporter molecules.

In another preferred embodiment, immunomagnetic particles, which include, for example, monoclonal or polyclonal antibodies specific for the target analyte, are added to the sample under conditions wherein the immunomagnetic particles bind to the target analyte. A magnetic field is applied to attract and hold the immunomagnetic particles and bound target analyte while unbound materials are removed, for example by washing. A phage modified to carry a reporter gene and to which has been attached an analyte-recognizing moiety is added to the sample. The analyte-recognizing moiety binds to the analyte. A helper strain of a microorganism susceptible to infection by the phage is added and a substrate that provides a signal in response to the reporter molecule are added. The phage replicates inside the microorganism producing the reporter molecule. The cells of the microorganism are then lysed to release the reporter molecules into the substrate and the presence or absence of the target analyte is detected. Under certain conditions, as an alternative to lysing the cells, the phage is allowed to replicate until the microorganisms burst and release the reporter molecules.

In a preferred embodiment, the reporter gene is the lacZ reporter gene, which codes for beta-galactosidase. The substrate is selected to release a signal in response to the presence of beta-galactosidase, and consists of any colorimetric substrate (i.e. o-nitrophenyl-$\beta$-D-galactoside (ONPG)), fluorescent substrate (i.e. 4-methyl-umbelliferyl-$\beta$-galactopyranoside), or via chemiluminescence of 1,2-dioxetan-galactopyranoside derivatives, or any other beta-galactosidase substrate.

DESCRIPTION OF THE INVENTION

Figure 1:
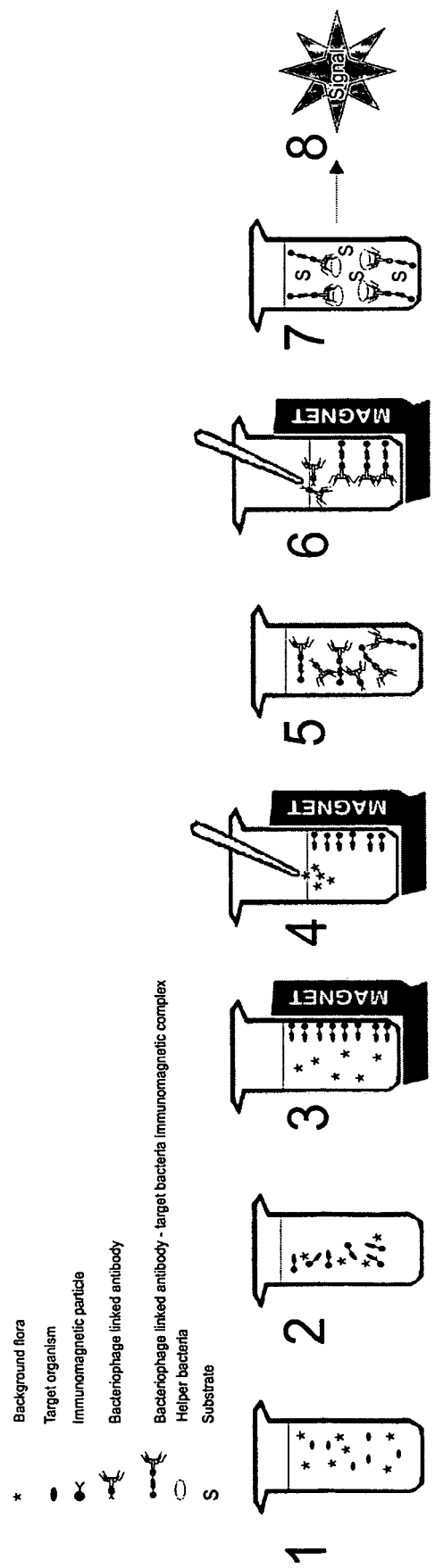
FIG. 1 is a schematic diagram of a bacteriophage linked immunosorbent assay according to the present invention.

In this disclosure, the term "bacteriophage" or "phage" include bacteriophage, mycophage, mycoplasma phage, mycobacteriaphage, and any other material comprising a virus that can invade bacteria, fungi, mycoplasmas, protozoa, or other microorganisms and use them to replicate itself.

In this disclosure, the term "immunomagnetic particles" includes paramagnetic beads coated with antibodies that will bind to antigens present on a target analyte thus capturing the target analyte and facilitate the concentration of these bead-attached analytes. The concentration process is created by a magnet placed on the side of the test tube bringing the beads to it.

The assays of the present invention consist of a reporter bacteriophage that has been genetically modified to carry the lacZ reporter gene, which encodes for β-galactosidase. The availability of the different classes of substrates (colorimetric, fluorescent, or luminescent) for β-galactosidase allows the BALISA to become extremely versatile. For example, if the BALISA was used in a field setting where it would be difficult to employ the use of instrumentation, the colorimetric substrate could be employed, enabling visual detection of the test result. If the reporter assay was conducted in a laboratory, where the use of instrumentation is more practical, the fluorescent or luminescent substrates could be utilized, allowing for more sensitive detection of the biomolecule in question. The reporter bacteriophage is further modified, such that any biomolecule binding moiety, such as an antibody or aptamer, is specifically attached to the capsid of the bacteriophage. The reporter bacteriophage remains infectious, because the ligand is specifically attached to the capsid (head of the bacteriophage), allowing the tail fibers to remain free. While the preferred embodiments of this invention call for the use of the lacZ reporter gene, those skilled in the art will recognize that other reporter genes can be successfully employed with this invention. The technology has been developed using bacteriophage T4, but any bacteriophage could be utilized in the BALISA.

Like an ELISA, a BALISA is an antibody sandwich capture assay in which one antibody is immobilized and serves to capture a ligand while a second antibody, which binds to a different epitope on the ligand, is used for quantitation. In ELISA, the second antibody is labeled with biotin so that a streptavidin/enzyme conjugate can be used to produce the signal. In BALISA, however, the second antibody is attached to the capsid of the reporter bacteriophage (to produce a bacteriophage linked antibody (BLA)). Therefore, when the secondary antibody binds to the target ligand, the reporter bacteriophage is also bound to the ligand via its capsid. After several wash steps to remove any unbound BLA, a helper bacteria (*E. coli* JM109 or similar lacZ- strain), and a β-galactosidase substrate is added. The reporter bacteriophage will infect the helper bacteria and produce copies of itself, and at the same time, produce multiple copies of β-galactosidase, which is detected by cleavage of the substrate.

The advantages of this system over other systems are numerous. The major advantage is sensitivity. Since the detection aspect of the assay is based on bacteriophage replication and enzymatic cleavage of a substrate, the assay has two built in signal amplification steps. It is clear that many bacteriophages can bind to a single target ligand. Therefore, the sensitivity of this assay should be vastly superior to other methods because as few as 100-1000 bacteriophages would be able to produce a detectable signal. In practical terms, this means that the system should be able to directly detect 10-100 particles of the target ligand, and the actual detection number is expected to be lower than that, since more than one bacteriophage will bind to a single ligand. In addition, the method described here, in which multiple assays can be produced from a single bacteriophage is advantageous, and cost effective, because the assays can be produced based on a standardized platform. Also, the choice of different substrates imparts a versatility on the BALISA not observed with other tests. The use of colorimetric substrates would allow for the test to be performed in the field without instrumentation. While the colorimetric substrates are the least sensitive, the bacteriophage amplification and enzymatic cleavage steps will still allow for sensitive detection of the target ligand. The luminescent substrates allow for extremely sensitive detection of the target ligand. The assay can be adapted so that it can be read using handheld luminometers, thereby allowing for very sensitive detection of the target ligand in the field. Handheld luminometers are already widely used in the pharmaceutical and food industries for hygiene monitoring.

Reporter bacteriophages represent a novel and sensitive alternative to conventional methods for the detection of bacteria within food. A bacteriophage (phage) is a virus that specifically infects bacteria, and a reporter gene is a segment of DNA that encodes for a protein that is easily measurable (i.e. a fluorescent protein or an enzyme). In this method, a bacteriophage is modified to carry a reporter gene. The reporter gene is introduced into a target bacterium via the bacteriophage during its normal infection cycle. Once the reporter gene has been introduced to the bacterium, it is expressed (i.e. the protein is produced), thereby allowing bacterial cells to be rapidly identified.

This technology is also broadly applicable to the detection of other bacterial foodborne pathogens, since another reporter phage with a different host range could be employed to detect other foodborne pathogens (i.e. *Salmonella* or *Listeria*), in the same one-tube format described here (see below). Also, since there are numerous calorimetric substrates for β-galactosidase, it will be possible to multiplex the assay to allow simultaneous detection of multiple pathogens.

The reporter bacteriophage technology described here is based on bacteriophage T4, which belongs to a super family of bacteriophages (the T even family) that infect many diverse bacteria, including pathogens that are the cause of food spoilage and human and animal illness. Therefore, it is possible to create multiple detection assays that specifically detect different bacterial pathogens, based on a single platform—the T4 bacteriophage.

The advantages of this system are numerous when compared to conventional techniques. First, the labor required is greatly reduced compared to those other methods because this technique is self-contained in one testing device. Second, the platform used in this technology, T4 bacteriophage with an integrated beta-galactosidase gene, allows for colorimetric detection of the signal making the test "instrumentless." Third, this technique is highly cost effective because multiple assays can be produced from a single bacteriophage. The assays can be produced based on a standardized platform, without the need to completely genetically and phenotypically characterize new bacteriophages for every new test. Finally, this technology eliminates many of the traditional reporter bacteriophage creation steps, uses a lytic bacteriophage (that cannot transfer virulence genes to the host), does not incorporate antibiotic resistance genes into the bacteriophage chromosome, and allows for the creation of multiple detection assays within a matter of weeks or months, rather than years using conventional methods.

In general, the invention entails the use of any bacteriophage modified to carry a reporter gene to which any analyte-recognizing moiety is attached. It will be recognized by one skilled in the art that analyte includes microorganisms, toxins, nucleic acids, etc. It will also be recognized by one skilled in the art that analyte-recognizing moieties include antibodies and apatamers, etc. The modified bacteriophage is used to attach to the target analyte, and this attachment is identified via bacteriophage amplification in a helper bacteria strain, and subsequent production and detection of the reporter gene.

In one example, a bacteriophage T4 strain carrying several genetic mutations is used. Specifically, the bacteriophage carries amber mutation in the genes denA and denB. These nonessential genes are responsible for degrading bacterial host and plasmid DNA upon infection of the host bacterial cell. This will result in much higher frequencies of homologous recombination between plasmid borne targets and the bacteriophage chromosome.

The bacteriophage has also been altered to carry a reporter gene. In this example, the reporter gene is a beta-galactosidase gene which has been fused, in frame, to the T4 promoter 22. The promoter 22/betagalactosidase fusion is stably integrated in a non-essential part of the T4 genome. The T4 reporter phage has a biotin-binding moiety incorporated into its capsid. This will allow the attachment of avidin or similar molecules to the T4 capsid. To accomplish the creation of detection assays that detect different analytes, monoclonal antibodies specific for the target analyte are biotinylated and attached to the T4 capsid via the biotin-avidin bridge. This results in a bacteriophage that has the ability to bind to the target analyte via its capsid, or head. The tail fibers face away from the analyte, so that the bacteriophage will remain infectious.

At this point, to detect the bound bacteriophage, a helper strain (*E. coli* JM109) and a substrate are simultaneously added to the assay. The analyte-bound bacteriophage then infects the helper bacteria and produces beta-galactosidase, which is detectable due to cleavage of the substrate.

The use of a beta-galactosidase gene in this example allows for colorimetric, fluorescent, or luminescent detection of the signal, making the test instrument-less (if colormetric substrate is used). This is an advantage over conventional rapid microbiological detection methods. Alternatively, if a luminescent substrate is used (which vastly increases the sensitivity of the assay), the test can be analyzed using a held-held luminometer, a device widely used in the food industry to rapidly monitor hygiene.

As an example, if a detection assay for *Salmonella* were desired, a *Salmonella* specific monoclonal antibody would be attached to the capsid of the T4 reporter bacteriophage, via the biotin-avidin bridge. *Salmonella* cells would be isolated from the food, environmental, or clinical samples via immuomagnetic separation. The reporter phage would be added to the separated *Salmonella* cells, and would bind to the *Salmonella* capsid first (via the antibody). After two wash steps to remove any unbound phage, the helper bacteria and substrate would be added to the tube. The bound phages would infect the helper bacteria, producing beta-galactosidase, which would become detectable upon cleavage of the substrate. Depending on the class of substrate used, detection could be visual (colormetric substrate), fluorescent, or luminescent in nature.

A preferred embodiment of the methods of this invention is illustrated in FIG. 1. In the initial step (1), a sample containing the target analyte (as well as background flora) is placed into a tube, or microtiter well. In the next step (2), immunomagnetic particles, specific for the target analyte, are added (alternatively, specific monoclonal or polyclonal antibodies could be attached to the walls and bottom of the tube/well). The immunomagnetic particles will specifically bind to the target analyte. Next (3), a magnet is applied, and the immunomagnetic particles, carrying with them the bound analyte, are attracted to the magnet. Then, in step (4), the background flora are removed, and a wash step is performed to remove any non-specifically bound background flora. In step (5), the bacteriophage linked antibody (BLA) is added. The BLA will bind capsid first (via the monoclonal antibody) to the target analyte. In the next step (6), the BLA, or target analyte, immunomagnetic particle complex is captured by the magnet, allowing any unbound BLAs to be removed. Several wash steps are performed to remove any unbound BLAs. In step (7), the helper bacteria are added. The bound BLAs will infect the helper bacteria, due to the ability of the bacteriophage to bind to the helper bacteria. The bacteriophage will replicate inside the helper bacteria, and force the helper bacteria to make the reporter gene (beta-galactosidase). Once the bacteriophage replication cycle is complete (1 hour), the helper bacteria may be actively lysed, releasing the beta-galactosidase. Alternatively, in appropriate circumstances, the phage may replicate until it ruptures the helper bacteria and releases the beta-galactosidase. The substrate is added at the same time as the helper bacteria. The substrate can be colorimetric, fluorescent, or luminescent in nature. Depending on the substrate, the required instrument (visual, fluorometer, luminometer) is used in step (8) to measure the signal.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

I claim:

1. A method of detecting the presence of absence of a target analyte in a sample, comprising:
    (a) providing in a receptacle containing the sample immunomagnetic particles capable of binding to the target analyte in the sample;
    (b) applying a magnetic field to attract and hold the immunomagnetic particles and bound target analyte;
    (c) removing unbound materials from the receptacle;
    (d) adding to the receptacle a bacteriophage modified to carry a reporter gene and an analyte-recognizing moiety under conditions wherein the bacteriophage will bind to the target analyte;
    (e) removing unbound materials from the receptacle;
    (f) adding microorganisms to the receptacle that can be infected by the bacteriophage and providing conditions under which the bacteriophage will infect the microorganisms and replicate inside the microorganism;
    (g) adding a detector substrate to the receptacle that generates a signal in the presence of the reporter molecule;
    (h) lysing the microorganisms to release the reporter molecule; and
    (i) detecting the presence or absence of the signal.

2. The method of claim 1, wherein the bacteriophage is T4.

3. The method of claim 1, wherein the reporter gene is beta-galactosidase.

4. The method of claim 1, wherein the analyte is selected from the group consisting of bacteria, viruses, toxins, spores, and prions.

* * * * *